US012076587B2

(12) United States Patent
Lansonneur et al.

(10) Patent No.: US 12,076,587 B2
(45) Date of Patent: Sep. 3, 2024

(54) DOSE SMEARING EFFECT MODELING FOR RADIATION TREATMENT PLAN

(71) Applicant: Siemens Healthineers International AG, Steinhausen (CH)

(72) Inventors: Pierre Lansonneur, Helsinki (FI); Perttu Niemela, Espoo (FI); Michiko Rossi, Espoo (FI); Matti Sakari Ropo, Helsinki (FI); Viljo Petaja, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 299 days.

(21) Appl. No.: 17/707,738

(22) Filed: Mar. 29, 2022

(65) Prior Publication Data

US 2023/0310887 A1    Oct. 5, 2023

(51) Int. Cl.
*A61N 5/10*    (2006.01)
(52) U.S. Cl.
CPC .... *A61N 5/1031* (2013.01); *A61N 2005/1034* (2013.01); *A61N 2005/1087* (2013.01)
(58) Field of Classification Search
CPC .......... A61N 5/1031; A61N 2005/1034; A61N 2005/1087
See application file for complete search history.

(56) References Cited

U.S. PATENT DOCUMENTS 8,716,663 B2 * 5/2014 Brusasco ............. A61N 5/1071
250/336.1
11,857,805 B2 * 1/2024 Purwar .................... H01J 35/14

FOREIGN PATENT DOCUMENTS

WO    WO-2018132847 A1 *    7/2018    ............... A61N 5/00

* cited by examiner

*Primary Examiner* — David P Porta
*Assistant Examiner* — Fani Polyzos Boosalis
(74) *Attorney, Agent, or Firm* — Harness, Dickey, & Pierce P.L.C

(57) ABSTRACT

A computer implemented method of developing a radiation treatment plan comprising spot scanning of a treatment target comprising accessing information associated with a patient and information pertaining to a radiation delivery machine. The method further comprises determining an area associated with the treatment target, wherein the area comprises a plurality of spots and computing a weighting for each spot of the plurality of spots, wherein the weighting is associated with a number of protons delivered at a respective spot. Further, the method comprises computing timing related parameters based on information retrieved from the radiation delivery machine and determining a transition dose delivered by the radiation delivery machine during the transition from one spot to another spot when irradiating the treatment target.

20 Claims, 8 Drawing Sheets

1

DOSE SMEARING EFFECT MODELING FOR RADIATION TREATMENT PLAN

TECHNICAL FIELD

This description relates generally to the field of radiation therapy, and more particularly to accurately modeling the execution of a radiation therapy treatment plan on a radiation therapy treatment system.

BACKGROUND

The use of radiation therapy to treat cancer is well known. Typically, radiation therapy involves directing a beam of high energy proton, photon, ion, or electron radiation into a target volume in a treatment target of unhealthy tissue (e.g., a tumor or lesion).

Radiation therapy treatment plan development generally employs medical imaging, such as X-ray, computed tomography (CT), magnetic resonance imaging (MM), or the like. Typically, a series of two-dimensional patient images, each representing a two-dimensional cross-sectional "slice" of the patient anatomy, are used to reconstruct a three-dimensional representation of a volume of interest (VOI), or structure of interest, from the patient anatomy.

The VOI typically includes one or more organs of interest, often including a planning target volume (PTV), such as a malignant growth or an organ including malignant tissue targeted for radiation therapy; a relatively healthy organ at risk (OAR) in the vicinity of a malignant growth at risk of radiation therapy exposure; or a larger portion of the patient anatomy that includes a combination of one or more PTVs along with one or more OARs. The objective of the radiation therapy treatment plan development typically aims to irradiate as much of the PTV as near the prescription dose as possible, while attempting to minimize irradiation of nearby OARs.

The resulting radiation therapy treatment plans are used during medical procedures to selectively expose precise areas of the body, such as malignant tumors, to specific doses of radiation in order to destroy the undesirable tissues. During the development of a patient-specific radiation therapy treatment plan, information generally is extracted from the three-dimensional model to determine parameters such as the shape, volume, location, and orientation of one or more PTVs along with one or more OARs.

Proton therapy is a type of external beam radiation therapy that is characterized by the use of a beam of protons to irradiate diseased tissue. Typically, radiation therapy involves directing a beam of high energy proton, photon, or electron radiation ("therapeutic radiation") into a target volume (e.g., a tumor or lesion). A chief advantage of proton therapy over other conventional therapies such as X-ray or neutron radiation therapies is that proton radiation can be limited by depth, and therefore the exposure to inadvertent radiation can be avoided or at least limited by non-target cells having a depth beyond a target calculated area. In other words, a proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The plan defines various aspects of the radiation therapy using simulations and optimizations that may be based on past experiences. For example, the plan can specify the appropriate beam type and the appropriate beam energy. Other parts of the plan can specify, for example, the angle of the beam relative to the patient, the beam shape, the placement of boluses and shields, and the like. In general, the purpose of the treatment plan is to deliver sufficient radiation to unhealthy tissue while minimizing exposure of surrounding healthy tissue to that radiation. Accurately modeling the dose distribution in spot scanning is critically important to a treatment planner.

One radiation therapy technique is known as spot scanning, also known as pencil beam scanning. In spot scanning, a beam is directed to spots in a treatment target as prescribed by the treatment plan. The prescribed spot locations are typically arranged in a fixed (raster) pattern for each energy layer of the beam, and the beam is delivered on a fixed scanning path within an energy layer. By superposition of several beams of different energies at neighboring spots, the Bragg peaks of the beams overlap to deliver the prescribed dose across the treatment target up to the edges of the target, with a sharp drop to zero dose beyond the edges.

A precise calculation of the number of spots and their placement (location and distribution) is important. The goal is to determine a spot placement that: conforms to the outline of the treatment target, to improve the lateral penumbra and spare healthy tissue outside the treatment target from exposure to radiation beyond what is necessary to treat the unhealthy tissue; and is uniform inside the treatment target, to avoid dose variations (dose inhomogeneity) inside the treatment target so that the prescribed dose is delivered to all parts of the target. When generating a treatment plan, an initial spot pattern or grid is specified for the entire treatment target, and the plan is optimized by adjusting the weights of the spots in the pattern.

One of the challenges that treatment planners have to contend with is modeling the cumulative effect of dose smearing resulting from transitioning the pencil beam from one spot to another. In pencil beam scanning, a proton beam is moved across the target volume (the VOI) using a pair of deflection magnets. In most cases, the treatment planning system models the dose delivery across the VOI by discretizing the dose into spots that are delivered one after another. However, at the machine level, if the distance between two consecutive spots is smaller than a certain limit, the dose is split into two components: and they are 1) the irradiation at the actual spot location and 2) the irradiation during the transitionary period when the beam is moving from one spot to the next. Because the time to move the beam from one spot to the other is typically small compared to the time needed to deliver the spot dose, commercially available conventional treatment planning systems model the cumulative dose for the treatment plan as the sum of the doses delivered at each of the individual spots. However, such modeling is not ideal because it does not take into account dose smearing effects and can lead to disadvantageous discrepancies between the planned dose distribution and the actual delivered dose distribution. This is especially pronounced with plans associated with ultra-high dose rate (FLASH radiation therapy) delivery.

SUMMARY

Embodiments according to the present invention provide a computer implemented methodology that models more accurate treatment plans by accounting for the radiation delivered during the transitionary period when a beam is moving from one spot to the next during spot scanning. By taking into account the cumulative dose smearing effect, a treatment planner is able to develop a more accurate dose distribution plan. In this way, embodiments of the present invention are able to reduce the discrepancy between the planned dose distribution and the actual delivered dose distribution.

In one embodiment, a computer implemented method of developing a radiation treatment plan comprising spot scanning of a treatment target is disclosed. The method comprises accessing information associated with a patient and information pertaining to a radiation delivery machine. The method further comprises determining an area associated with the treatment target, wherein the area comprises a plurality of spots and computing a weighting for each spot of the plurality of spots, wherein the weighting is associated with a number of protons delivered at a respective spot. Further, the method comprises computing timing related parameters based on information retrieved from the radiation delivery machine and determining a transition dose delivered by the radiation delivery machine during the transition from one spot to another spot when irradiating the treatment target.

In another embodiment, a computer system comprising a processor coupled to a bus and memory coupled to said bus wherein said memory is programmed with instructions that when executed cause said computer system to implement a method of developing a radiation treatment plan comprising spot scanning of a treatment target is disclosed. The method comprises accessing information associated with a patient and information pertaining to a radiation delivery machine. The method further comprises determining an area associated with the treatment target, wherein the area comprises a plurality of spots. The method also comprises computing a weighting for each spot of the plurality of spots, wherein the weighting is associated with a number of protons delivered at a respective spot. Further, the method comprises computing timing related parameters based on information retrieved from the radiation delivery machine and computing a dose delivered at each spot of the plurality of spots. Finally, the method comprises determining a plurality of transition doses delivered by the radiation delivery machine, wherein the plurality of transition doses comprise a radiation delivered during each transition from one spot to another spot when irradiating the treatment target.

In one embodiment, a non-transitory computer-readable storage medium having computer-executable instructions for causing a computer system to perform a method of developing a radiation treatment plan comprising spot scanning of a treatment target is disclosed. The method comprises accessing information associated with a patient and information pertaining to a radiation delivery machine. The method further comprises determining an area associated with the treatment target, wherein the area comprises a plurality of spots and computing a weighting for each spot of the plurality of spots, wherein the weighting is associated with a number of protons delivered at a respective spot. Further, the method comprises computing timing related parameters based on information retrieved from the radiation delivery machine and determining a transition dose delivered by the radiation delivery machine during the transition from one spot to another spot when irradiating the treatment target.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
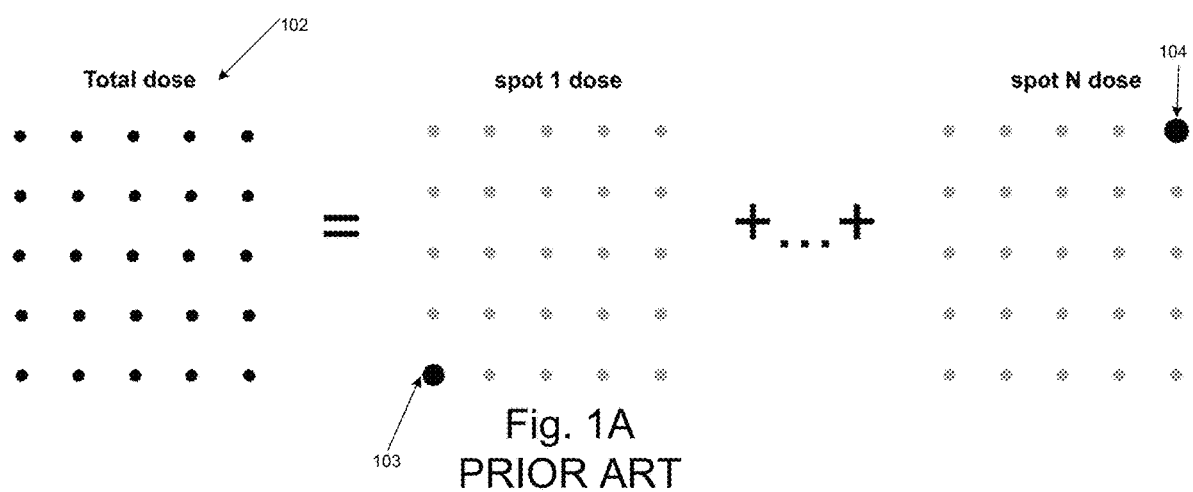
FIG. 1A illustrates a conventional model of a dose distribution across a VOI.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "computing," "determining," "accumulating," or the like, refer to actions and processes (e.g., the flowcharts of FIG. 8) of a computing system or similar electronic computing device or processor (e.g., the computing system 200 of FIG. 2). The computing system or similar electronic computing device manipulates and transforms data represented as physical (electronic) quantities within the computing system memories, registers or other such information storage, transmission or display devices.

Portions of the detailed description that follows are presented and discussed in terms of a method. Although steps and sequencing thereof are disclosed in figures herein (e.g., FIG. 8) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Dose Smearing Effect Modeling for Radiation Treatment Plan

This present disclosure provides a solution to the challenge of accurately modeling the dose distribution for a radiation treatment plan comprising spot scanning of a treatment target. As mentioned earlier, one of the challenges that treatment planners have to contend with is modeling the cumulative effect of the dose smearing resulting from transitioning the pencil beam from one spot to another. The treatment planning system models the dose delivery across the VOI by discretizing the dose into spots that are delivered one after another. However, at the machine level, if the distance between two consecutive spots is smaller than a certain limit, the dose is split into two components: and they are 1) the irradiation at the actual spot location and 2) the irradiation during the transitionary period when the beam is moving from one spot to the next. Because the time to move the beam from one spot to the other is typically small compared to the time needed to deliver the spot dose, commercially available treatment planning systems model the cumulative dose for the treatment plan as the sum of the doses delivered at each of the individual spots. In other words, conventional treatment planning systems ignore the dose delivered between consecutive spots in spot scanning.

FIG. 1A illustrates a conventional model of a dose distribution across a VOL As shown in FIG. 1, a conventional model of a dose distribution discretizes the total dose 102 into spots that are delivered one after another. Accordingly, the total dose can be computed as the sum of the dose of each of the discrete spots, from spot 1 103 to spot N 104.

Figure 1B:
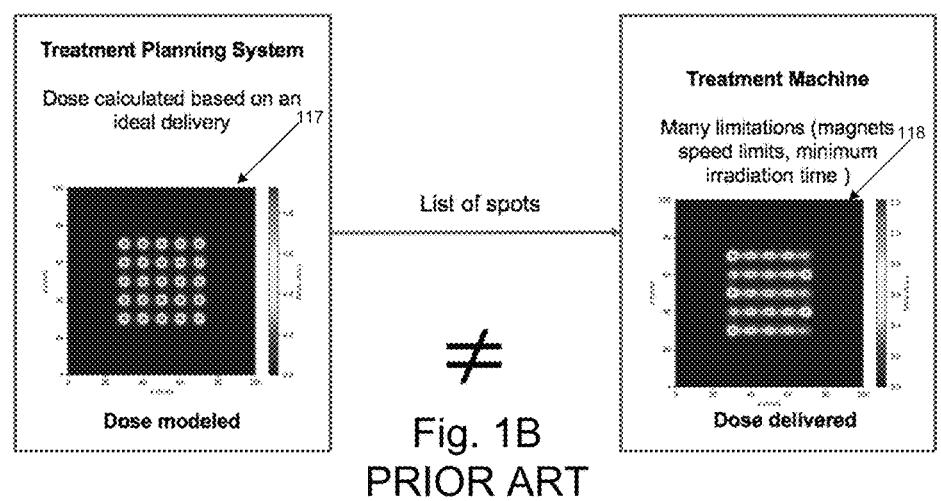
FIG. 1B illustrates the manner in which a dose calculated based on ideal delivery conditions may differ from the actual dose delivered in a conventional treatment planning system.

However, conventional modeling is not ideal because it does not take into account dose smearing effects and can lead to discrepancies between the planned dose distribution and the actual delivered dose distribution. This is especially pronounced with plans associated with ultra-high dose rate (FLASH radiation therapy) delivery. FIG. 1B illustrates the manner in which a dose calculated based on ideal delivery conditions may disadvantageously differ from the actual dose delivered in a conventional treatment planning system. As shown in FIG. 1B, conventional treatment planning systems calculate a dose based on an ideal delivery 117 where only the irradiation at the actual spot location is taken into account. The actual dose delivery 118 varies, however, because of limitations of the treatment machine, e.g., magnet speed limits, minimum irradiation times, etc. This results in discrepancies because the irradiation during the transitionary period when the beam is moving from one spot to the next (which may be a result of machine limitations) is not taken into account.

Embodiments according to the present invention provide a methodology that models more accurate treatment plans by accounting for the irradiation during the transitionary period when a beam is moving from one spot to the next during spot scanning. By taking into account the cumulative dose smearing effect, a treatment planner is able to develop a more accurate dose distribution plan. In this way, embodiments of the present invention are able to reduce the discrepancy between the planned dose distribution and the actual delivered dose distribution. In order to provide a better modeling of planned delivery, embodiments of the present invention rely on planning information and line scanning information.

Figure 2:
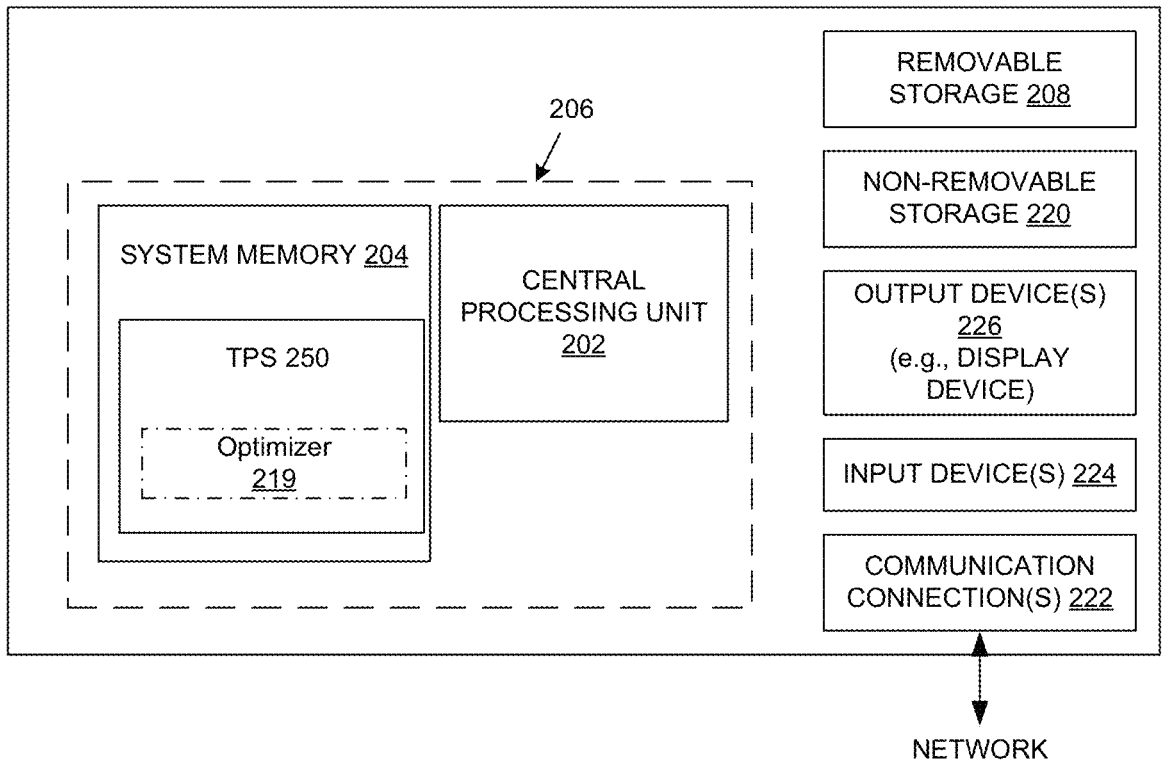
FIG. 2 shows a block diagram of an example of a computing system upon which the embodiments described herein may be implemented.

FIG. 2 shows a block diagram of an example of a computing system 200 upon which the embodiments described herein may be implemented within a treatment system. In its most basic configuration, the system 200 includes at least one processing unit 202 and memory 204. This most basic configuration is illustrated in FIG. 2 by dashed line 206. The system 200 may also have additional features and/or functionality. For example, the system 200 may also include additional storage (removable and/or non-removable) including, but not limited to, magnetic or optical disks or tape. Such additional storage is illustrated in FIG. 2 by removable storage 208 and non-removable storage 220. The system 200 may also contain communications connection(s) 222 that allow the device to communicate with other devices, e.g., in a networked environment using logical connections to one or more remote computers.

The system 200 also includes input device(s) 224 such as keyboard, mouse, pen, voice input device, touch input device, etc. Output device(s) 226 such as a display device, speakers, printer, etc., may also be included.

In the example of FIG. 2, the memory 204 includes computer-readable instructions, data structures, program modules, and the like associated with a treatment planning system 250, which include an optimizer 219. However, the treatment planning system 250 may instead reside in any one of the computer storage media used by the computer system 200, or may be distributed over some combination of the computer storage media, or may be distributed over some combination of networked computers. The treatment planning system 250 is used to evaluate and produce a final (prescribed) treatment plan.

As will be explained further below, embodiments according to the invention utilize an optimizer 219 to more accurately model the dose distribution in spot scanning plans. The optimizer 219 does this by more accurately modeling the irradiation during the transitionary period when a beam is moving from one spot to the next during spot scanning. By taking into consideration the cumulative dose smearing effects (comprised of all the partial doses delivered during the transition of the beam from one discrete spot to the next), the optimizer is able to develop a more reliable model for the dose distribution in spot scanning plans.

Figures 3A, 3B:
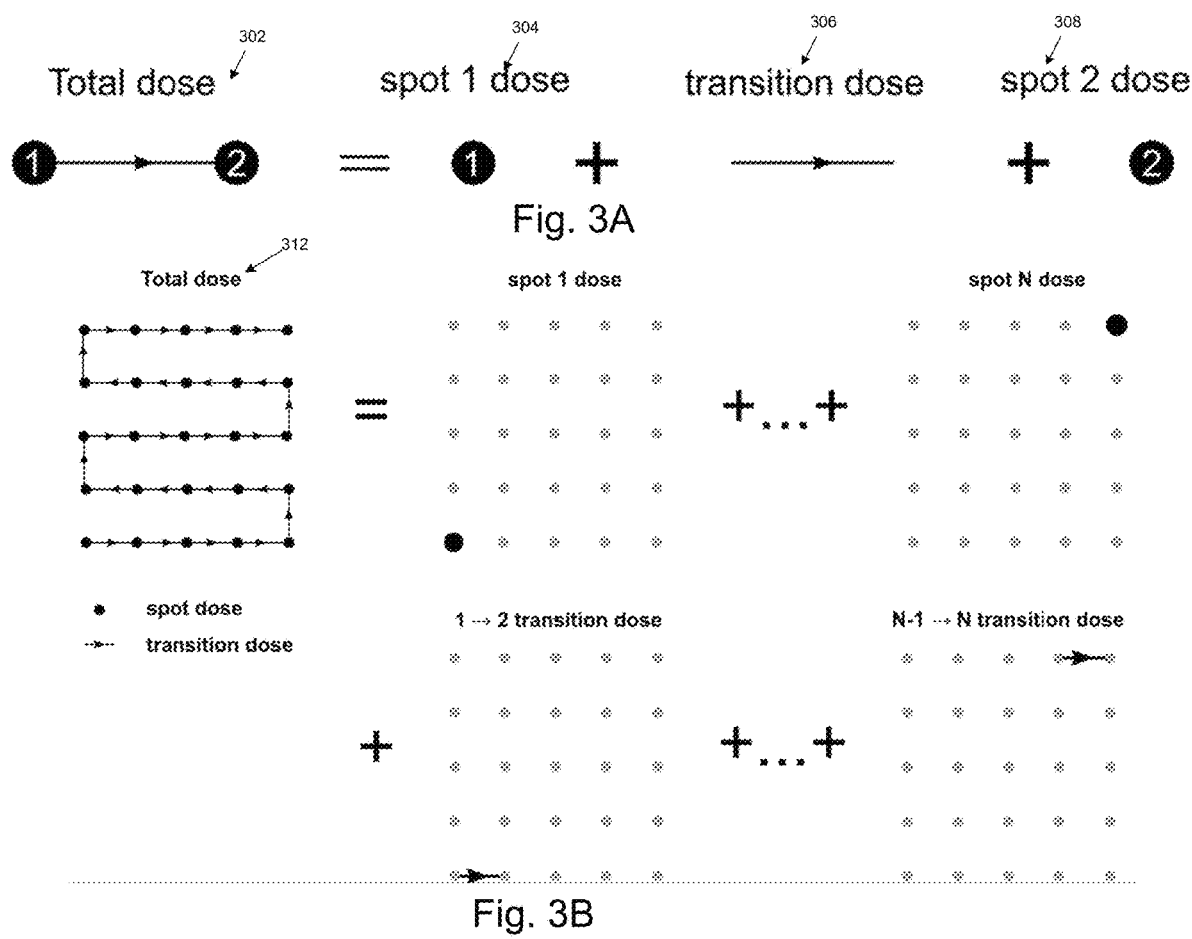
FIG. 3A illustrates the manner in which an accurate total dose is computed in accordance with an embodiment of the present invention.
FIG. 3B illustrates a model of a dose distribution across a VOI that accounts for the radiation delivered during the transition between spots when performing spot scanning in accordance with an embodiment of the present invention.

FIG. 3A illustrates the manner in which an accurate total dose is computed in accordance with an embodiment of the present invention. As shown in FIG. 3A, in order to accurately compute the total dose 302 delivered in spot scanning plans, the treatment planner needs to account for not only the dose delivered at the spots (e.g., the spot 1 dose 304 and the spot 2 dose 308) but also the transition dose 306 delivered when transitioning the beam from spot 1 to spot 2.

FIG. 3B illustrates a model of a dose distribution across a VOI that accounts for the radiation delivered during the transition between spots when performing spot scanning in accordance with an embodiment of the present invention. As shown in FIG. 3B, the total dose 312 delivered can be modeled as the sum of the dose delivered at all the spots (spot 1, spot 2 . . . spot N) and all the transition doses delivered when moving the beam between spots (spot 1→2, spot 2→3, . . . spot N−1→N).

In conventional commercially available treatment planning systems, the dose matrix for a field is calculated by summing the matrices of each individual spots as shown in equation 1.1 below. In other words, a dose is decomposed as a sum of the contribution of each of the individual spots.

$$D = \Sigma_{j=1}^{N} D_j, \text{ where } D \text{ is the dose matrix} \quad (1.1)$$

The dose matrix for a spot j is calculated by multiplying the influence matrix (also known as the dose matrix) $d_j$ with the spot weight as shown in equation 1.2 below.

$$D_j = d_j W_j. \quad (1.2)$$

Note that in equation 1.2 above, $d_j$ is the dose matrix for spot j and $W_j$ is the total number of protons (weight) as conventionally computed in the treatment planning system.

As mentioned earlier, unlike conventional modeling systems (associated with equations 1.1 and 1.2 above) embodiments of the present invention split the total dose into individual spot doses and the dose resulting from transitioning the beam from one spot to another (also known as the dose smear effect).

Embodiments of the present invention model the total dose for a field in accordance with equations 2.1 and 2.2 below.

$$D = D_1 + D_{1 \to 2} + D_2 \quad (2.1)$$

Note that $D_{1 \to 2}$ in equation 2.1 above is the dose matrix for the transition between spot 1 and spot 2. Breaking down equation 2.1 into the spot weights results in equation 2.2 below.

$$D = w_1 \cdot d_1 + w_{1 \to 2} \cdot d_{1 \to 2} + w_2 \cdot d_2 \quad (2.2)$$

Note that in equation 2.2 above, $w_j$ is the number of protons delivered at spot j coordinates; $d_j$ is the dose matrix for spot j; $d_{1 \to 2}$ is the dose matrix for the transition (between spot 1 and spot 2); and $w_{j \to j+1}$ is the number of protons delivered when the beam is moved between spot j and spot j+1. (e.g., $w_{1 \to 2}$ is the number of protons delivered when transitioning between spot 1 and spot 2).

For purposes of the discussion herein, a constant beam intensity is assumed. However, embodiments of the present invention may use similar principles with a varying beam intensity as well. A constant beam intensity results in equation 2.3 below.

$$\text{Beam Intensity} = \frac{w_j}{t_j} = \frac{w_{j \to j+1}}{t_{j \to j+1}} = \frac{w_j + w_{j \to j+1}}{t_j + t_{j \to j+1}} = \frac{W_j}{T_j} \quad (2.3)$$

In equation 2.3 above, $w_j$ is the number of protons delivered at spot j coordinates; $t_j$ is the time spent when the beam is maintained at spot j coordinates; $t_{j \to j+1}$ is the time needed to move the beam from spot j to spot j+1; $T_j = t_j + t_{j \to j+1}$ is the total irradiation time for spot j; $w_{j \to j+1}$ is the total number of spots delivered between spot j to spot j+1; and $W_j = w_j + w_{j \to j+1}$ is the total number of protons (weight) as currently implemented in the treatment planning system.

Using equation 2.3 above, the irradiation time at spot 1 ($t_j$) and the irradiation time in between spot 1 and spot 2 ($t_{j \to j+1}$) can be introduced into equation 2.2, resulting in equation 2.4 below.

$$D = \frac{t_1}{T_1} \cdot W_1 \cdot d_1 + \frac{t_{1 \to 2}}{T_1} \cdot W_1 \cdot d_{1 \to 2} + \frac{t_2}{T_2} \cdot W_2 \cdot d_2 \quad (2.4)$$

Note that the terms $W_1$, $d_1$, $W_2$ and $d_2$ are typically computed for conventional treatment planning systems related to spot scanning techniques, where $W_1$ is the weight (e.g. number of protons delivered) at spot 1, $W_2$ is the weight at spot 2, $d_1$ is the dose matrix associated with spot 1 and $d_2$ is the dose matrix associated with spot 2.

The timing related terms, $t_1$, $t_2$, $t_{1 \to 2}$, $T_1$ and $T_2$ are not tracked by conventional treatment planning systems because they do not track dose smearing effects. The term $t_1$ is the irradiation time at spot 1, the term $t_2$ is the irradiation time at spot 2, the term $t_{1 \to 2}$ is the irradiation time in between the two spots, the term $T_1$ is the total time associate with spot 1 and the term $T_2$ is the total time associated with spot 2. Embodiments of the present invention model the timing terms $t_1$, $T_1$, $t_2$, $T_2$, $t_{1 \to 2}$ using information collected from the machine implementing the treatment plan and can depend on several machine dependent factors, e.g., speed of machine electronics, response time of the magnets in the spot scanning system, etc. The timing terms can then be used as machine delivery parameters when modeling the delivery dose in the treatment planning system. In an embodiment, the timing terms can be derived from line scanning modeling.

By way of example, in one type of proton beam, the shortest spot duration may be $t_1+t_{1\to2}=2.5$ ms. For two spots spaced 10 mm apart (which is the maximum distance before the beam is turned off), the time to move from current spot to the next spot $t_{1\to2}$ scanning along the X direction (slowest direction) may be as long as 2 ms. The relative importance of smearing can accordingly be fairly high. Note that proton beams may evolve toward even shorter spot duration and larger spacing in future releases, making the effect even more pronounced.

Thereafter, embodiments of the present invention can compute $d_{1\to2}$, which is the smeared dose matrix for the transition between spots 1 in a variety of ways. The smeared dose matrix may be computed in a variety of different ways.

In one embodiment, the smeared dose matrix may be computed by modeling the transition dose as a series of a finite number of virtual spots on the line that the proton beam is moving. In other words, the fluence of a constantly moving proton beam is approximated with a set of virtual spots placed equidistantly between the end points of the line. Using a higher number of virtual spots along the line results in a more accurate model.

In another embodiment, therefore, the smeared dose may be computed by modeling the transition dose as a series of infinite number of virtual spots on the line that the proton beam is moving. In the limit of infinite number of virtual spots, the total proton fluence of at an arbitrary spatial location $\vec{r}_z$ (on a plane z perpendicular to beam direction) is described by the following integral (or summation):

$$f_{1\to2}(\vec{r}_z)=\int_0^1 F_s[\vec{r}_z;\vec{r}_{z1}+\gamma\cdot(\vec{r}_{z2}-\vec{r}_{z1})]d\gamma \quad (3.1)$$

In equation 3.1 above, $f_s[\vec{r}_z; \vec{r}_{z0}]$ is the fluence at location $\vec{r}_z$ contributed by a single spot centered at $\vec{r}_{0z}$. The locations $\vec{r}_{1z}$ and $\vec{r}_{2z}$ and are the locations of spots 1 and 2, projected on plane z. The dose matrix $d_{1\to2}$ is then calculated from the fluence in a similar way as for spots.

In a different embodiment, statistical modeling may be used to compute the total proton fluence. For example, Monte Carlo dose calculation can be carried out (e.g., also by using equation 3.1) and interpreting the resulting fluence (F) as the position-direction distribution (phase-space) of protons on plane z. The dose $d_{1\to2}$ is then calculated through randomized sampling of particles from this distribution.

Figure 4:
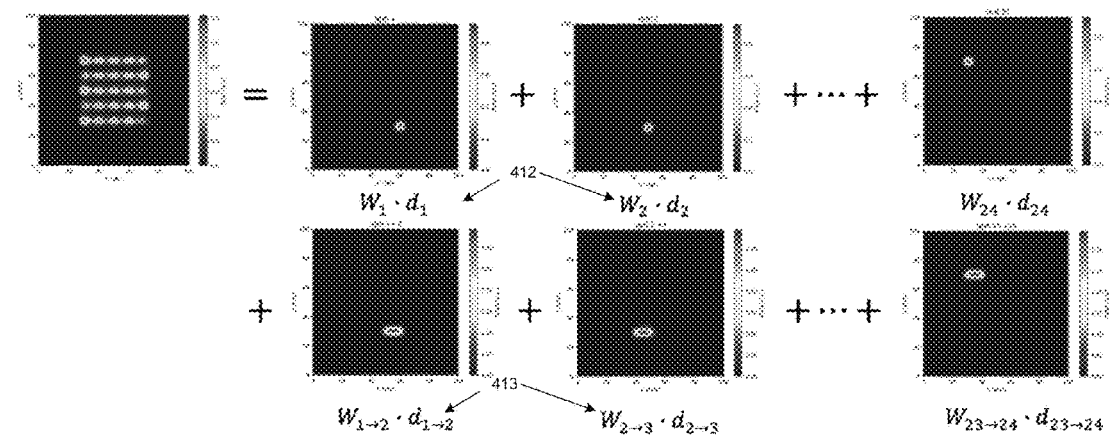
FIG. 4 illustrates the manner in which a generalized influence matrix is computed in accordance with an embodiment of the present invention.

When the transition dose matrix for each of the transition doses is determined, the treatment planner is able to develop a more accurate delivered dose distribution by summing up the radiation delivered at each of the individual spots and the radiation delivered during the transitions between spots. FIG. 4 illustrates the manner in which a generalized influence matrix is computed in accordance with an embodiment of the present invention. The elements of the generalized influence matrix ($GIM_{ij}$) are the dose resulting from the transition from spot i to spot j, with the diagonal elements being the spot dose. The generalized influence matrix computed by a treatment planning system designed in accordance with embodiments of the present invention takes into account the individual spot doses 412 and the smeared doses 413.

In one embodiment, each individual component or element of the generalized influence matrix (e.g., each of the individual spot doses or each of the discrete smeared doses) may be computed and stored separately in the treatment planning system and used by the optimizer 219 in the treatment planning system 250. The optimizer 219 is is able to evaluate doses of multiple variations of the plan in order to find the optimal treatment plan. Given access to each individual component of the generalized influence matrix, the optimizer 219 is able to evaluate the dose delivery distribution regardless of the order in which the dose is delivered.

Figure 5:
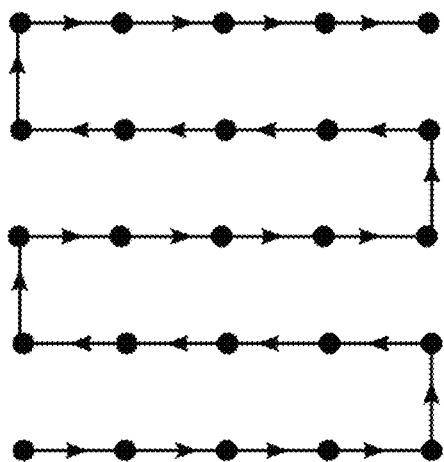
FIG. 5 illustrates a manner in which dose delivery may be computed for variations of a treatment plan in accordance with an embodiment of the present invention.
Figure 5:
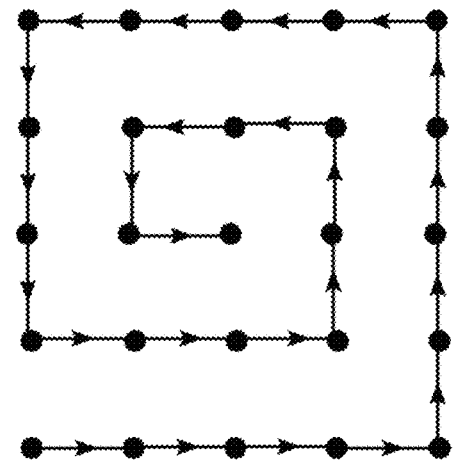

FIG. 5 illustrates a manner in which dose delivery may be computed for variations of a treatment plan in accordance with an embodiment of the present invention. As shown in FIG. 5, the dose delivery order may be different even where the spots in the target treatment plan are identically positioned. For example, even though both spot positions 512 and 514 are the same, the dose delivery pattern results in a different dose distribution across the targets. Because the optimizer 219 can generate a generalized influence matrix, it can determine the dose distribution accurately for all possible patterns or orders in which the dose may be delivered. This is important because the scanning pattern may make a difference in the way the dose is administered to a patient and the impact it has on the patient. Embodiments of the present invention are advantageously able to compute a generalized influence matrix and an accurate resulting dose distribution for any dose delivery pattern. Conventional treatment planning system would compute identical generalized influence matrices for both spot positions 512 and 514 because they did not take into account the dose smear effects.

Figure 6:
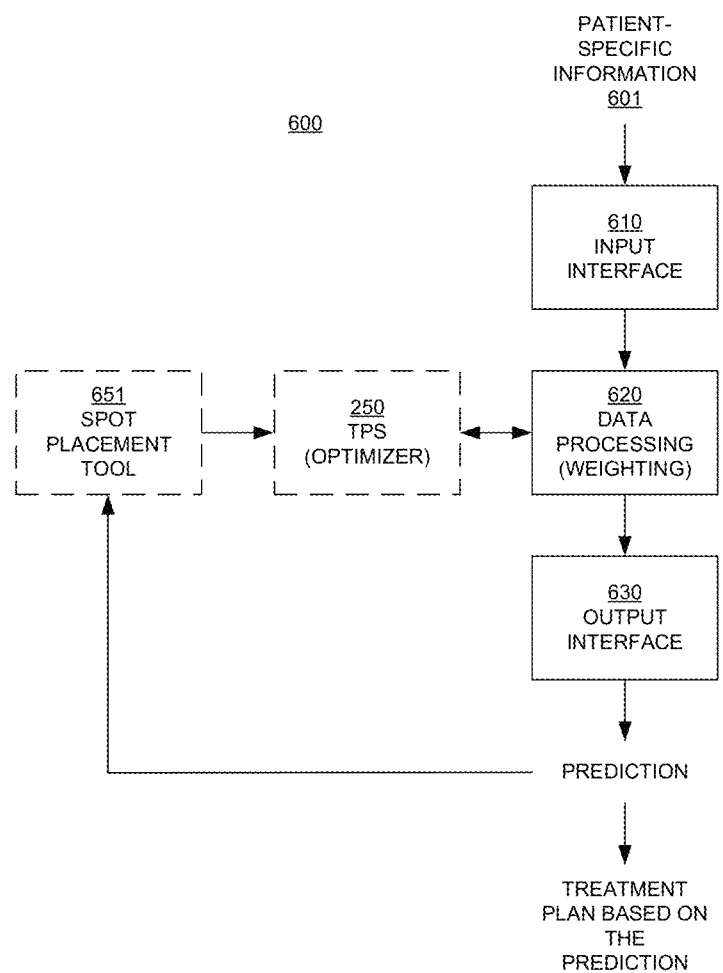
FIG. 6 is a block diagram illustrating an example of an automated radiation therapy treatment planning system with which the embodiments described herein may be implemented.

FIG. 6 is a block diagram illustrating an example of an automated radiation therapy treatment planning system 600 with and on which the embodiments described herein may be implemented. The system 600 includes an input interface 610 to receive patient-specific information (data) 601, a data processing component 620 ("computer system") that implements the treatment planning system 250, and an output interface 630. The system 600 in whole or in part may be implemented as a software program, hardware logic, or a combination thereof on/using the computer system 200 (FIG. 2).

In the example of FIG. 6, the patient-specific information 601 is provided to and processed by the treatment planning system 250, which yields a prediction result. A proposed radiation treatment plan based on the prediction result can then be generated.

The inputs to the data processing component 620 (e.g., the treatment planning system 250) include an initial pattern (or grid or placement) of spots in the treatment target. The initial spot pattern may itself be generated by a spot placement tool 651 that is coupled to or is a component of the treatment planning system 250. In embodiments according to the disclosed invention, the initial spot pattern for optimization in the treatment planning system 250 considers or is based on the size and/or shape of the treatment target. The treatment planning system 250 can then adjust the weights of the spots with respect to, for example, beam energy or dose rate. The goal is to determine a set of weights so that, during treatment, the treatment target will receive a homogenous dose (a uniform dose across the treatment target) and the delivered dose will conform more closely to the edges of the treatment target.

More specifically, the proposed radiation treatment plan is evaluated to determine whether or not objectives (e.g., clinical goals) that are specified for treatment of a patient are satisfied by the proposed radiation treatment plan. The clinical goals or objectives may be expressed in terms of a set of quality metrics, such as target homogeneity, conformity to the treatment target, critical organ sparing, and the like, with respective target values for the metrics.

Figure 7:
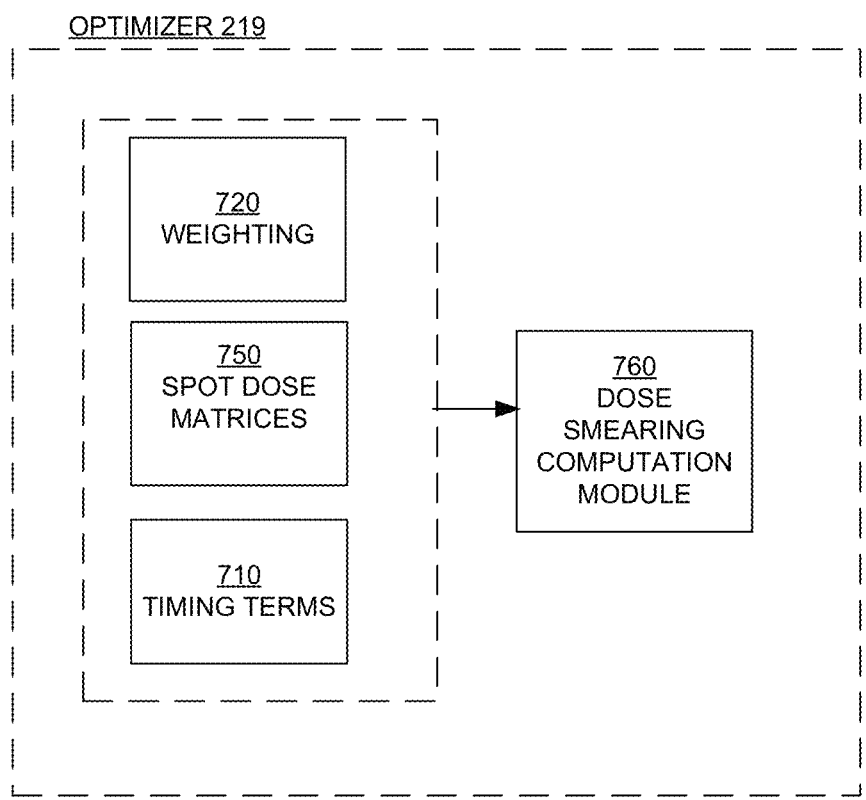
FIG. 7 is a block diagram illustrating exemplary components of the optimizer with which the embodiments described herein may be implemented.

FIG. 7 is a block diagram illustrating exemplary components of the optimizer 219 with which the embodiments described herein may be implemented. In one embodiment, the weighting module 720 may be part of the optimizer module 219. The weighting module is able to determine and adjust the weights of the spots with respect to, for example, beam energy or dose rate. The weighting of a spot is associated with the number of protons to be delivered to the spot. The $W_j$ for each of the spots may be determined by the weighting module 720. It should be noted that the weighting module 720 may also be implemented within the treatment planning system 250 in general and is not limited to being part of the optimizer 219.

Spot dose matrices may be computed by module 750. Module 750 determines the $d_j$ for each of the spots. In one embodiment, both the dose matrices and the weighting terms may be determined by the weighting module 720. In other words, both functions may be performed by the same module.

In one embodiment, the timing related terms may be computed by module 710. As noted above, module 710 collects information from the machine implementing the treatment plan and the timing terms computed can depend on several machine dependent factors, e.g., speed of machine electronics, response time of the magnets in the spot scanning system, etc. In one embodiment, timing information may be computed based on machine-specific parameters.

In one embodiment, the dose smearing matrix (e.g., $d_{i \to j}$) for each of the transitions in the generalized influence matrix may be computed by module 760, which uses information from modules 720, 710 and 750.

Figure 8:
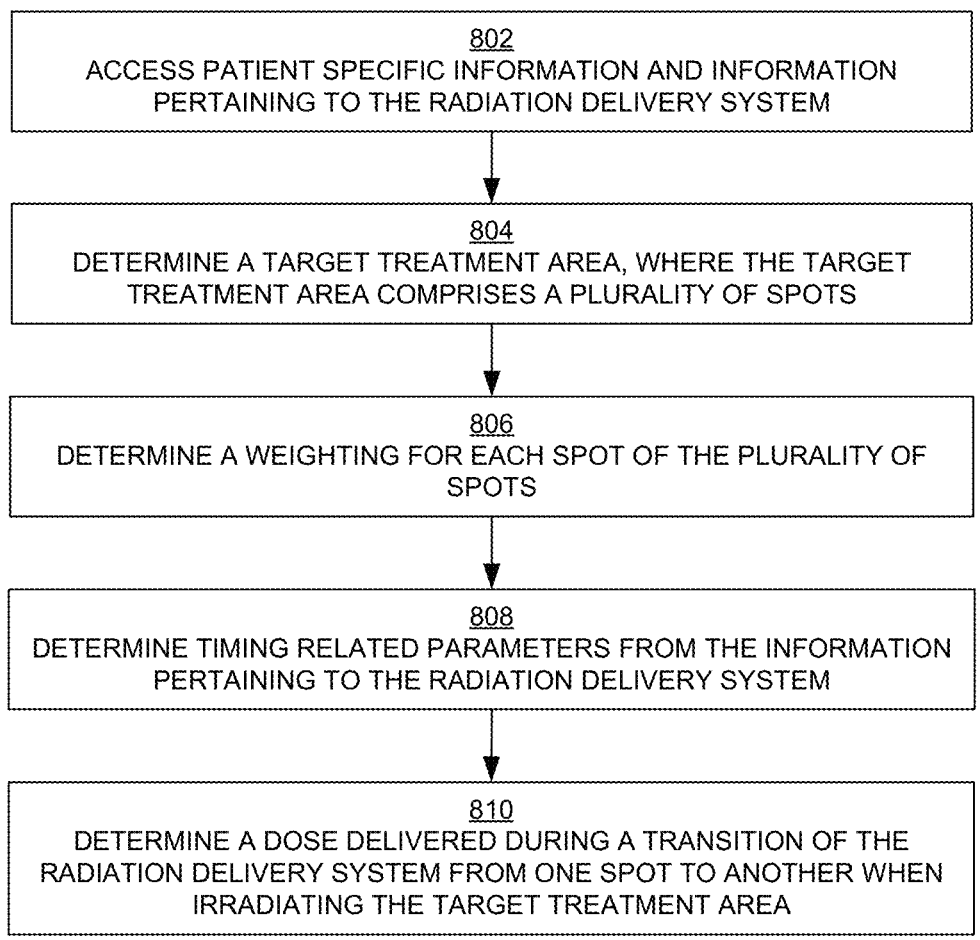
FIG. 8 is a flowchart depicting another exemplary computer implemented process flow for planning a radiation treatment comprising spot scanning of a treatment target, in accordance with an embodiment of the present invention.

FIG. 8 is a flowchart depicting another exemplary process flow 800 for planning a radiation treatment comprising spot scanning of a treatment target, in accordance with an embodiment of the present invention.

At step 802, patient specific information and information pertaining to the radiation delivery system are accessed from a data store.

At step 804, a target treatment area is determined, where the target treatment area comprises a plurality of spots.

At step 806, a weighting is determined for each spot of the plurality of spots, where the weighting is associated with a number of protons delivered at the respective spot. In one embodiment, a dose matrix for each of the spots in addition to the weighting is also determined.

At step 808, timing related parameters are extracted from the information pertaining to the radiation delivery system.

At step 810, a dose delivered during a transition of the radiation delivery system from one spot to another when irradiating the target treatment area is determined. In one embodiment, all the transition doses in the treatment area are computed and added to all the individual spot doses in order to determine a total dose distribution for a treatment plan.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer implemented method of developing a radiation treatment plan comprising spot scanning of a treatment target, said method comprising:
   accessing information associated with a patient and information pertaining to a radiation delivery machine;
   determining an area associated with the treatment target, wherein the area comprises a plurality of spots;
   computing a weighting for each spot of the plurality of spots, wherein the weighting is associated with a number of protons delivered at a respective spot;
   computing timing related parameters based on information retrieved from the radiation delivery machine; and
   determining a transition dose delivered by the radiation delivery machine during a transition from one spot to another spot when irradiating the treatment target under the radiation treatment plan.

2. The method of claim 1, further comprising:
   determining a spot dose for each spot of the plurality of spots; and
   computing a total dose distribution for the radiation treatment plan by accumulating a spot dose determined for each spot of the plurality of spots and a transition dose determined for each transition from one spot to another during the irradiating under the treatment plan.

3. The method of claim 1, wherein the determining the transition dose comprises determining a transmission dose matrix by modeling a line associated with the transition from the one spot to the another spot as a series of finite spots.

4. The method of claim 1, wherein the determining the transition dose comprises determining a transmission dose matrix by modeling a line associated with the transition from the one spot to the another spot as a summation of a series of infinite spots.

5. The method of claim 1, wherein the determining the transition dose comprises:
   modeling a line associated with the transition from the one spot to the another spot as a summation of a series of infinite spots; and
   performing a statistical computation to determine a transition dose matrix associated with the transition dose.

6. The method of claim 5, wherein the statistical computation is a Monte Carlo calculation.

7. The method of claim 1, further comprising:
   determining a spot dose for each spot of the plurality of spots; and
   computing a total dose distribution for the radiation treatment plan by accumulating a spot dose determined for each spot of the plurality of spots and a transition dose determined for each transition from one spot to another during the irradiating, wherein the total dose distribution depends on a pattern followed by the radiation delivery machine during the irradiating.

8. A computer system comprising a processor coupled to a bus and memory coupled to said bus, wherein said memory is programmed with instructions that when executed cause said computer system to implement a method of developing a radiation treatment plan comprising spot scanning of a treatment target, wherein said method comprises:
   accessing information associated with a patient and information pertaining to a radiation delivery machine;
   determining an area associated with the treatment target, wherein the area comprises a plurality of spots;
   computing a weighting for each spot of the plurality of spots, wherein the weighting is associated with a number of protons delivered at a respective spot;

computing timing related parameters based on information retrieved from the radiation delivery machine;
computing a dose delivered at each spot of the plurality of spots; and
determining a plurality of transition doses delivered by the radiation delivery machine, wherein the plurality of transition doses comprise a radiation delivered during each transition from one spot to another spot when irradiating the treatment target under the radiation treatment plan.

9. The computer system of claim 8, wherein the method further comprises:
determining a total dose distribution by summing up the plurality of transition doses with the dose delivered at each respective spot of the plurality of spots.

10. The computer system of claim 8, wherein the determining the plurality of transition doses comprises determining a transmission dose matrix for each transition by modeling a line associated with a respective transition as a series of finite spots.

11. The computer system of claim 8, wherein the determining the plurality of transition doses comprises determining a transmission dose matrix for each transition by modeling a line associated with a respective transition as a summation of a series of infinite spots.

12. The computer system of claim 8, wherein the determining the plurality of transition doses comprises:
modeling a line associated with each transition as a summation of a series of infinite spots; and
performing a statistical computation to determine a transition dose matrix associated with each transition.

13. The computer system of claim 8, wherein the statistical computation is a Monte Carlo calculation.

14. A non-transitory computer-readable storage medium having computer-executable instructions for causing a computer system to perform a method of developing a radiation treatment plan comprising spot scanning of a treatment target, the method comprising:
accessing information associated with a patient and information pertaining to a radiation delivery machine;
determining an area associated with the treatment target, wherein the area comprises a plurality of spots;
computing a weighting for each spot of the plurality of spots, wherein the weighting is associated with a number of protons delivered at a respective spot;
computing timing related parameters based on information retrieved from the radiation delivery machine; and
determining a transition dose delivered by the radiation delivery machine during a transition between spots when irradiating the treatment target under the treatment plan.

15. The non-transitory computer-readable storage medium of claim 14, wherein the method further comprises:
determining a spot dose for each spot of the plurality of spots; and
computing a total dose distribution for the radiation treatment plan by accumulating a spot dose determined for each spot of the plurality of spots and a transition dose determined for each transition between spots during the irradiating.

16. The non-transitory computer-readable storage medium of claim 14, wherein the determining the transition dose comprises determining a transmission dose matrix by modeling a line associated with the transition between spots as a series of finite spots.

17. The non-transitory computer-readable storage medium of claim 14, wherein the determining the transition dose comprises determining a transmission dose matrix by modeling a line associated with the transition between spots as a summation of a series of infinite spots.

18. The non-transitory computer-readable storage medium of claim 14, wherein the determining the transition dose comprises:
modeling a line associated with the transition as a summation of a series of infinite spots; and
performing a statistical computation to determine a transition dose matrix associated with the transition dose.

19. The non-transitory computer-readable storage medium of claim 18, wherein the statistical computation is a Monte Carlo calculation.

20. The non-transitory computer-readable storage medium of claim 14, wherein the method further comprises:
determining a spot dose for each spot of the plurality of spots; and
computing a total dose distribution for the radiation treatment plan by accumulating a spot dose determined for each spot of the plurality of spots and a transition dose determined for each transition between spots during the irradiating, wherein the total dose distribution depends on a pattern followed by the radiation delivery machine during the irradiating.

* * * * *